(12) United States Patent
Dourval et al.

(10) Patent No.: US 12,376,165 B2
(45) Date of Patent: Jul. 29, 2025

(54) PAIRING WITH AN ASPIRATING SMOKE DETECTOR DEVICE

(71) Applicant: Honeywell International Inc., Charlotte, NC (US)

(72) Inventors: Clement Dourval, Charlotte, NC (US); Dino Petronio, Trieste (IT); Simone Gasparella, Trieste (IT)

(73) Assignee: Honeywell International Inc., Charlotte, NC (US)

( * ) Notice: Subject to any disclaimer, the term of this patent is extended or adjusted under 35 U.S.C. 154(b) by 551 days.

(21) Appl. No.: 17/469,544

(22) Filed: Sep. 8, 2021

(65) Prior Publication Data

US 2023/0074864 A1    Mar. 9, 2023

(51) Int. Cl.
*H04W 76/14* (2018.01)
*G01N 33/00* (2006.01)
*G08B 17/10* (2006.01)

(52) U.S. Cl.
CPC ........ *H04W 76/14* (2018.02); *G01N 33/0073* (2013.01); *G08B 17/10* (2013.01)

(58) Field of Classification Search
CPC ... H04W 76/14; H04W 12/047; H04W 12/50; G01N 33/0073; G08B 17/10
See application file for complete search history.

(56) References Cited

U.S. PATENT DOCUMENTS

| 8,711,656 | B1 | 4/2014 | Paulson | |
|---|---|---|---|---|
| 9,250,299 | B1* | 2/2016 | Yarlagadda | ............ G01D 21/02 |
| 10,601,523 | B1 | 3/2020 | Abhishek | |
| 2007/0116293 | A1 | 5/2007 | Busser et al. | |
| 2013/0223279 | A1* | 8/2013 | Tinnakornsrisuphap | H04L 41/0809 370/254 |
| 2014/0068744 | A1* | 3/2014 | Bran | ...................... H04W 12/50 726/9 |

(Continued)

FOREIGN PATENT DOCUMENTS

| CN | 110636456 | 12/2019 | |
|---|---|---|---|
| JP | 7001683 B2 * | 1/2022 | .......... F24F 11/0008 |

(Continued)

OTHER PUBLICATIONS

Dunn, Caroline. "How to Setup Google Nest Protect Smoke Detector." YouTube, YouTube, Dec. 29, 2020, www.youtube.com/watch?v=HbjEmEZggYs. (Year: 2020).*

(Continued)

*Primary Examiner* — Austin J Moreau
(74) *Attorney, Agent, or Firm* — Brooks, Cameron & Huebsch, PLLC

(57) ABSTRACT

Methods, devices, and systems for pairing with an aspirating smoke detector device are described herein. One device includes a wireless module, a buzzer; and a controller. The wireless module can be configured to receive a connection request from a mobile device, and the controller can be configured to generate a temporary key (TK) having a plurality of digits, cause the buzzer to produce a buzzer signal including a plurality of portions corresponding to the plurality of digits of the TK, receive, via the wireless module, an indication of the TK determined by the mobile device based on the buzzer signal, and communicate with the mobile device to complete a pairing with the mobile device using the TK.

19 Claims, 5 Drawing Sheets

(56) References Cited

U.S. PATENT DOCUMENTS

| | | |
|---|---|---|
| 2015/0099466 A1 | 4/2015 | Narendra et al. |
| 2016/0029114 A1* | 1/2016 | Chen ................ H04W 4/80 |
| | | 381/74 |
| 2016/0253887 A1 | 9/2016 | Webb |
| 2017/0111937 A1 | 4/2017 | Chen et al. |
| 2018/0336332 A1* | 11/2018 | Singh ................ H04L 63/18 |
| 2019/0166502 A1* | 5/2019 | Chaskar .............. H04W 12/122 |
| 2020/0037159 A1* | 1/2020 | Jones ................ H04B 11/00 |
| 2020/0402381 A1* | 12/2020 | Nelson ................ G08B 7/06 |
| 2023/0325486 A1* | 10/2023 | Park ................ G06F 21/60 |
| | | 726/18 |

FOREIGN PATENT DOCUMENTS

| | | | |
|---|---|---|---|
| TW | 568306 | 1/2017 | |
| WO | WO-2018044471 A1 * | 3/2018 | ............. E21B 47/14 |

OTHER PUBLICATIONS

Jake. "Transmitting Data with Sound." YouTube, YouTube, Sep. 29, 2018, www.youtube.com/watch?v=Uke4EOqQ9J4. (Year: 2018).*

* cited by examiner

PAIRING WITH AN ASPIRATING SMOKE DETECTOR DEVICE

TECHNICAL FIELD

The present disclosure relates to methods, devices, and systems for pairing with an aspirating smoke detector device.

BACKGROUND

Large facilities (e.g., buildings), such as commercial facilities, office buildings, hospitals, and the like, may have an alarm system that can be triggered during an emergency situation (e.g., a fire) to warn occupants to evacuate. For example, an alarm system may include a control panel (e.g., a fire control panel) and a plurality of aspirating smoke detector devices located throughout the facility (e.g., on different floors and/or in different rooms of the facility) that detect a hazard event, such as smoke generation (e.g., as the result of a fire or otherwise). The aspirating smoke detector can transmit a signal to the control panel in order to notify a building manager, occupants of the facility, emergency services, and/or others of the hazard event via alarms or other mechanisms.

DETAILED DESCRIPTION

Figure 1:
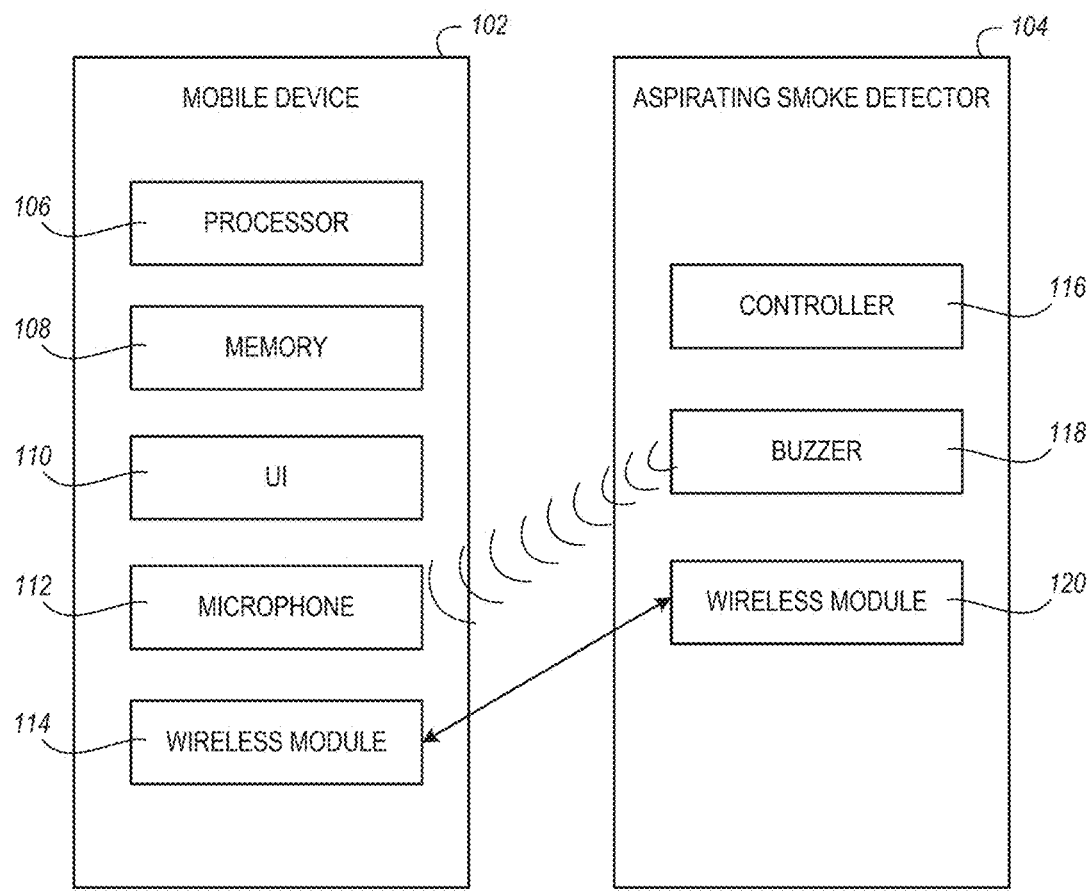
FIG. 1 illustrates a system 100 for pairing with an aspirating smoke detector device 104 in accordance with one or more embodiments of the present disclosure.

Methods, devices, and systems for pairing with an aspirating smoke detector device are described herein. One device includes a wireless module, a buzzer; and a controller. The wireless module can be configured to receive a connection request from a mobile device, and the controller can be configured to generate a temporary key (TK) having a plurality of digits, cause the buzzer to produce a buzzer signal including a plurality of portions corresponding to the plurality of digits of the TK, receive, via the wireless module, an indication of the TK determined by the mobile device based on the buzzer signal, and communicate with the mobile device to complete a pairing with the mobile device using the TK.

An aspirating smoke detector device can be utilized in a facility to detect a hazard event by detecting the presence of smoke. The aspirating smoke detector device can draw gas (e.g., air, via a blower) from the facility into a sensor through a network of pipes throughout the facility. The sensor can sample the gas in order to determine whether the gas includes smoke particles. In response to detection of smoke particles, the aspirating smoke detector device can transmit a signal to a control panel in the facility to signal detection of smoke particles.

An aspirating smoke detector device may monitor various operational parameters associated with the aspirating smoke detector device. For example, the aspirating smoke detector device may monitor a blower speed of a blower of the aspirating smoke detector device, an air flow rate of gas through the aspirating smoke detector device, an air flow temperature of gas through the aspirating smoke detector device, and/or a smoke level of gas through the aspirating smoke detector device, among other operational parameters associated with the aspirating smoke detector device.

Such operational parameters may provide insight to a user regarding the aspirating smoke detector device. For example, it may be beneficial for a user to monitor and/or review the operational parameters of the aspirating smoke detector device in order to determine a state of the aspirating smoke detector device, determine whether the aspirating smoke detector device may have detected smoke (e.g., related to a fire event or other event), predict issues relating to the aspirating smoke detector device and/or the aspirating smoke detection system in the facility, among other information.

However, in many cases, aspirating smoke detector devices (hereinafter sometimes referred to simply as "detectors") may lack the functionality to directly communicate operational parameters to a user. This may be especially true for more inexpensive detectors. For instance, some detectors may lack a display altogether. Some detectors may be equipped with only a set of light emitting diodes (LEDs) and/or buttons. As a result, users attempting to visualize operational parameters may be stymied, especially if those users are inexperienced and/or unfamiliar with the detector. In addition, with such limited user functionality, commissioning, maintaining, and/or upgrading such detectors may be difficult.

Though detectors may provide limited direct user interaction, they may include a wireless module that allows them to communicate with a device (e.g., a mobile device) that can provide enhanced functionality. In some cases, for instance, detectors include a Bluetooth® module that enables pairing with a mobile device.

Pairing a detector with a mobile device having an enhanced user interface can allow a user to quickly determine the status of an aspirating smoke detector device in the facility and generate awareness regarding facility safety. Further, the user may modify operational parameters of the aspirating smoke detector device via the user interface. Such presentation and modification functionality can allow for a robust but easy to understand presentation of hazard detection information.

However, pairing with detectors in a facility presents heightened security risks compared to pairing with devices like wireless headphones, for instance. Cybersecurity is becoming increasingly important for connected devices. Architectures are becoming more sophisticated while cybersecurity is trying to adapt in fire detection systems. The slow adoption of security controls and defense measures may leave facilities vulnerable. In order to use Bluetooth connectivity safely, a safe and secure pairing method is desirable and may even be mandated in some facilities and/or jurisdictions. Safety and security, however, often carry undesirable price tags.

Embodiments of the present disclosure provide a secure pairing method between mobile devices and detectors without the need to alter or upgrade existing detectors and incur the costs associated therewith. For instance, embodiments herein can utilize the controllers (e.g., RX113 microcontrollers) of existing detectors. Embodiments herein can avoid adding extra hardware (e.g., displays, keyboards, etc.) to detectors. As a result, the functionality of detectors can be greatly—and securely—expanded, while the costs are kept at a reasonable level.

In accordance with the present disclosure, security is provided by an out-of-band (OOB) pairing method. In some embodiments, for instance, a noise-generating component (hereinafter referred to as a "buzzer") of a detector can be operated at different frequencies to communicate an audio signal that can be received (e.g., "heard") by a microphone of a mobile device. The signal can include a plurality of portions that correspond to a plurality of digits of a Temporary Key (TK). For example, a buzzer can buzz at a first frequency, then a second, then a third, then a fourth, then a fifth, and then a sixth. The mobile device can receive these different frequencies and translate them to the digits (e.g., 0 through 9) of the TK. With both devices having the TK, those of skill in the art will appreciate that the Bluetooth pairing process can proceed to completion. Once the devices are paired, the vast functionality provided by an application of the mobile device can enhance the value and the effectiveness of a facility's alarm system.

In the following detailed description, reference is made to the accompanying drawings that form a part hereof. The drawings show by way of illustration how one or more embodiments of the disclosure may be practiced.

These embodiments are described in sufficient detail to enable those of ordinary skill in the art to practice one or more embodiments of this disclosure. It is to be understood that other embodiments may be utilized and that process, electrical, and/or structural changes may be made without departing from the scope of the present disclosure.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

The figures herein follow a numbering convention in which the first digit or digits correspond to the drawing figure number and the remaining digits identify an element or component in the drawing. Similar elements or components between different figures may be identified by the use of similar digits. For example, 102 may reference element "02" in FIG. 1, and a similar element may be referenced as 302 in FIG. 3.

FIG. 1 illustrates a system 100 for pairing with an aspirating smoke detector device 104 in accordance with one or more embodiments of the present disclosure. As illustrated in FIG. 1, the system 100 includes a mobile device 102 and a detector 104.

The mobile device 102 can include a processor 106, a memory 108, a user interface (UI) 110, a microphone 112, and a wireless module 114. The detector 104 can include a controller 116, a buzzer 118, and a wireless module 120.

The detector 104 can be an aspirating smoke detector device. The controller 116 can be a microcontroller (e.g., a RX113 microcontroller), though embodiments herein are not so limited. In some embodiments, the controller lacks any security features. For example, the controller may employ no encryption techniques or tamper detection circuitry. The controller 116 can include a low speed on-chip oscillator. The controller 116 can have logic to perform various functions as described herein. It is noted, however, that the where the controller 116 is discussed, the detector 104 can be implemented with a processor and a memory having executable instructions (e.g., as described below in connection with the mobile device 102). The buzzer 118 is a component configured to alarm occupants of a facility of a hazard event. It is noted that while the term "buzzer" is used herein, embodiments of the present disclosure are not limited to particular types of components configured to alarm users. The buzzer 118 can be an electrical or electromechanical device, similar to a bell, that makes a buzzing noise and is used for signaling. In some embodiments, the buzzer 118 is a piezoelectric buzzer. A piezoelectric element may be driven by an oscillating electronic circuit or other audio signal source, driven with a piezoelectric audio amplifier. A piezoelectric buzzer can include acoustic cavity resonance or Helmholtz resonance to produce an audible beep.

The wireless module 120 can be a Bluetooth Low Energy (BLE) module, in some embodiments. The wireless module allows wireless communication with other devices capable of wireless communication. In some embodiments, for instance, the wireless module can be a radio transceiver mounted on a chip. In some embodiments, the detector 104 does not include a display.

The mobile device 102 can be, for example, a device that is (or can be) carried and/or worn by a user. For example, the mobile device 102 can be a phone (e.g., a smart phone), a tablet, a personal digital assistant (PDA), smart glasses, and/or a wrist-worn device (e.g., a smart watch), among other types of mobile devices.

The memory 108 can be any type of storage medium that can be accessed by the processor 106 to perform various examples of the present disclosure. For example, the memory 108 can be a non-transitory computer readable medium having computer readable instructions (e.g., computer program instructions) stored thereon that are executable by the processor 106 for pairing with an aspirating smoke detector device in accordance with the present disclosure.

The memory 108 can be volatile or nonvolatile memory. The memory 108 can also be removable (e.g., portable) memory, or non-removable (e.g., internal) memory. For example, the memory 108 can be random access memory (RAM) (e.g., dynamic random access memory (DRAM) and/or phase change random access memory (PCRAM)), read-only memory (ROM) (e.g., electrically erasable programmable read-only memory (EEPROM) and/or compact-disc read-only memory (CD-ROM)), flash memory, a laser disc, a digital versatile disc (DVD) or other optical storage, and/or a magnetic medium such as magnetic cassettes, tapes, or disks, among other types of memory.

Further, although memory 108 is illustrated as being located within mobile device 102, embodiments of the present disclosure are not so limited. For example, memory 108 can also be located internal to another computing resource (e.g., enabling computer readable instructions to be downloaded over the Internet or another wired or wireless connection).

The mobile device 102 can be connected to the detector 104 via the wireless module 114 and the wireless module 120. As previously discussed, the mobile device 102 can be wirelessly connected to the detector device 104 via a Bluetooth connection. As shown in FIG. 1, the mobile device 102 can include a microphone 112. The microphone 112 is a component (e.g., a transducer) that converts sound into an electrical signal. The microphone 112 can be any suitable microphone that is configured to convert sounds of the different frequencies produced by the buzzer 118 into electrical signals.

As illustrated in FIG. 1, the mobile device 102 includes a UI 110. For example, the UI 110 can display operational information associated with the detector 104 in a display. A user (e.g., operator) of the mobile device 102 can interact with the mobile device 102 via the UI 110. For example, the UI 110 can provide (e.g., display and/or present) information to the user of mobile device 102, and/or receive information from (e.g., input by) the user of mobile device 102. For instance, in some embodiments, UI 110 can be a graphical user interface (GUI) that can provide and/or receive information to and/or from the user of the mobile device 102. The display can be, for instance, a touch-screen (e.g., the GUI can include touch-screen capabilities). Alternatively, a display can include a television, computer monitor, mobile device screen, other type of display device, or any combination thereof, connected to the mobile device 102 and configured to receive a video signal output from the mobile device 102. The UI 110 can be localized to any language. For example, the UI 110 can display information in any language, such as English, Spanish, German, French, Mandarin, Arabic, Japanese, Hindi, etc.

Figure 2A:
FIG. 2A is an illustration of a display provided on a user interface associated with pairing with an aspirating smoke detector device in accordance with one or more embodiments of the present disclosure.
Figure 2B:
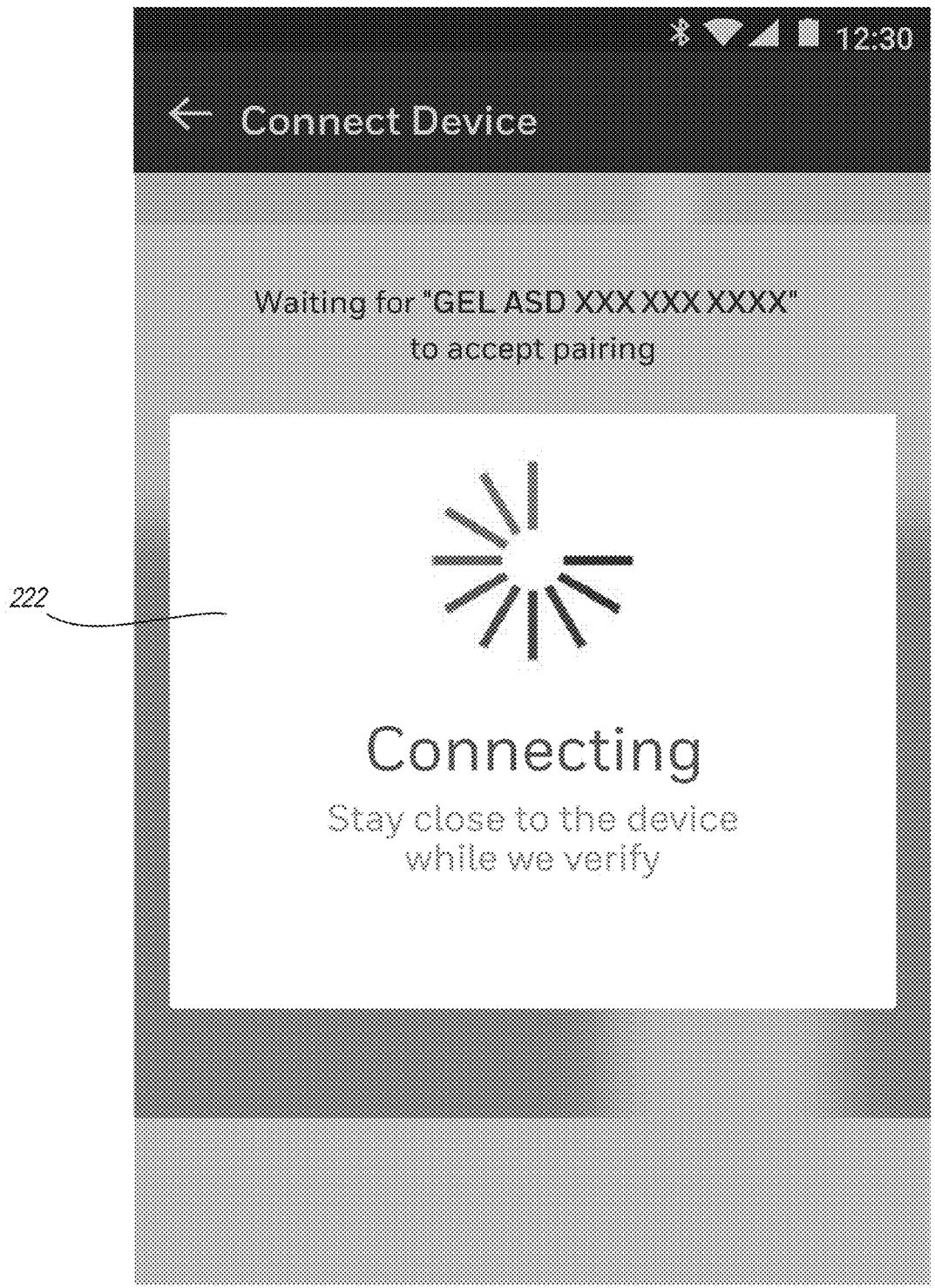
FIG. 2B is an illustration of another display provided on a user interface associated with pairing with an aspirating smoke detector device in accordance with one or more embodiments of the present disclosure.

FIG. 2A is an illustration of a display provided on a user interface associated with pairing with an aspirating smoke detector device in accordance with one or more embodiments of the present disclosure. FIG. 2B is an illustration of another display provided on a user interface associated with pairing with an aspirating smoke detector device in accordance with one or more embodiments of the present disclosure. FIGS. 2A and 2B are collectively referred to herein as "FIG. 2." It is noted that occasional reference back to FIG. 1 may be made throughout the present disclosure.

While only one detector 204 (e.g., "GEL ASK XXXX-XXXX-XXXX") is displayed in FIG. 1, the mobile device 102 can connect to various different detectors. The mobile device 102 may display, on the user interface 110, detectors which are within a threshold distance of the mobile device 102. The mobile device 102 may connect to the detector in response to a user selecting the "Pair Device" button 221 via the user interface 110.

As illustrated in FIG. 2B, a user has selected detector 204 to pair with, and a notification 222 is displayed indicating that a connection request has been sent from the mobile device 102. As known to those of skill in the art, a Bluetooth pairing process can begin when the initiating device (e.g., the mobile device 102) sends a connection request (e.g., "pairing request" to the other device (e.g., the detector 104). The two devices then exchange I/O capabilities, authentication requirements, maximum link key size and bonding requirements. Data being exchanged during this phase is typically unencrypted.

Figure 3:
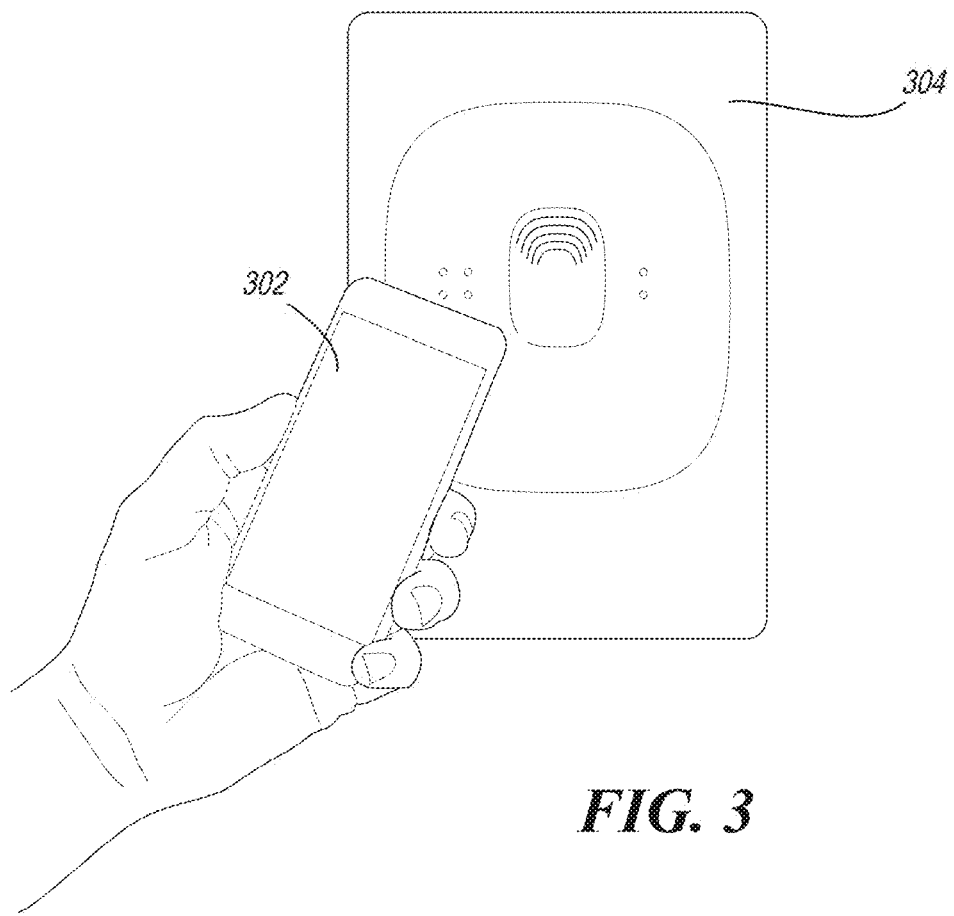
FIG. 3 is an illustration of a display provided on a user interface with a notification associated with positioning the mobile device with respect to the aspirating smoke detector in accordance with one or more embodiments of the present disclosure.

FIG. 3 is an illustration of a display provided on a user interface with a notification associated with positioning the mobile device with respect to the aspirating smoke detector in accordance with one or more embodiments of the present disclosure.

As known to those of skill in the art, once the initial phase of pairing is complete, the devices to be paired generate and/or exchange a TK using a pairing method. The two devices can then exchange Confirm and Rand values in order to verify that they both are using the same TK. Once this has been determined, the devices can use the TK along with the Rand values to create a Short Term Key (STK). The STK is then used to encrypt the connection.

As previously discussed, the pairing method described herein is an OOB method. After receiving the connection request, the controller 116 can generate a TK. The TK includes a plurality of digits. In some embodiments, the TK includes six digits. Each of the six digits can be selected from a group ranging from 0-9 (e.g., 0, 1, 2, 3, 4, 5, 6, 7, 8, or 9). In some embodiments, the TK is generated using a suitable random number generator. In some embodiments the TK is generated using the tolerance of the low speed on-chip oscillator of the detector.

Once the TK is generated, the controller 116 can translate the TK into a buzzer signal. A buzzer signal, as referred to herein, is a sequence of a plurality of audio signals (e.g., buzzes) that corresponds to the plurality of digits of the TK. As previously discussed, the buzzer 118 can buzz at different frequencies. Certain frequencies are associated with certain values of the portions of the buzzer signal. In an example, a frequency of 2.7 kHz corresponds to the number "9," 1.8 kHz corresponds to the number 8, and 1.2 kHz corresponds to the number 7. Thus, a TK of "987987" can be translated into a buzzer signal that includes a first portion during which the buzzer buzzes at 2.7 kHz, followed by a second portion during which the buzzer buzzes at 1.8 kHz, followed by a third portion during which the buzzer buzzes at 1.2 kHz, followed by a fourth portion during which the buzzer buzzes at 2.7 kHz, followed by a fifth portion during which the buzzer buzzes at 1.8 kHz, followed by a sixth portion during which the buzzer buzzes at 1.2 kHz. The particular frequencies (or frequency ranges) that correspond to the different TK digits may be user-configurable, in some embodiments. The duration of the buzzer signal, and the portions thereof, may be user-configurable.

While the buzzer 118 is buzzing, the display illustrated in FIG. 3 may be presented via the UI 110. The display can include a notification associated with positioning the mobile device 302 (e.g., the microphone 112 of the mobile device 302) with respect to the detector 304 while the buzzer signal is being produced. In some embodiments, the notification may indicate a particular distance within which the user should position the mobile device 302. In one example, the user may be notified to position the mobile device 302 within 30 centimeters of the detector 304. In another example, the user may be notified to position the mobile device 302 within 2 meters of the detector 304. In another example, the user may be notified to position the mobile device 302 within 3 meters of the detector 304. It should be appreciated that as security concerns increase, the volume of the buzzer 118 may be reduced and the corresponding distance may be shortened.

As previously discussed, the microphone 112 of the mobile device 102 can receive the buzzer signal. The mobile device 102 can determine the TK based on the received buzzer signal. Determining the TK can include determining a respective frequency of each of the plurality of portions. In some embodiments, the mobile device can compare the determined frequencies of the plurality of portions to a data structure (e.g., a table) that relates a plurality of different frequency ranges to a plurality of TK digits. Such a structure can be stored in the memory 108 of the mobile device 102, for instance. The structure can include a first frequency range corresponding to a first TK digit (e.g., 0), a second frequency range corresponding to a second TK digit (e.g., 1), a third frequency range corresponding to a third TK digit (e.g., 2), a fourth frequency range corresponding to a fourth TK digit (e.g., 3), a fifth frequency range corresponding to a fifth TK digit (e.g., 4), a sixth frequency range corresponding to a sixth TK digit (e.g., 5), a seventh frequency range corresponding to a seventh TK digit (e.g., 6), an eighth frequency range corresponding to an eighth TK digit (e.g., 7), a ninth frequency range corresponding to a ninth TK digit (e.g., 8), and a tenth frequency range corresponding to a tenth TK digit (e.g., 9). To illustrate, a received frequency that falls within the ninth frequency range indicates the ninth TK digit.

Accordingly, the mobile device 102 can determine the TK based on the buzzer signal and indicate that determined TK back to the detector 104. As previously discussed, pairing can then be completed through a process where the TK along with the Rand values are used to create the STK, which is then used to encrypt the connection. A successful pairing of the mobile device 102 and the detector 104 can be indicated on the display of the mobile device. In some embodiments, a particular frequency buzzed by the buzzer (or a particular sequence of buzzes by the buzzer) can additionally be used to indicate a successful pairing. In some embodiments, the detector 104 may include one or more LEDs, which can be used to indicate a successful pairing.

Figure 4:
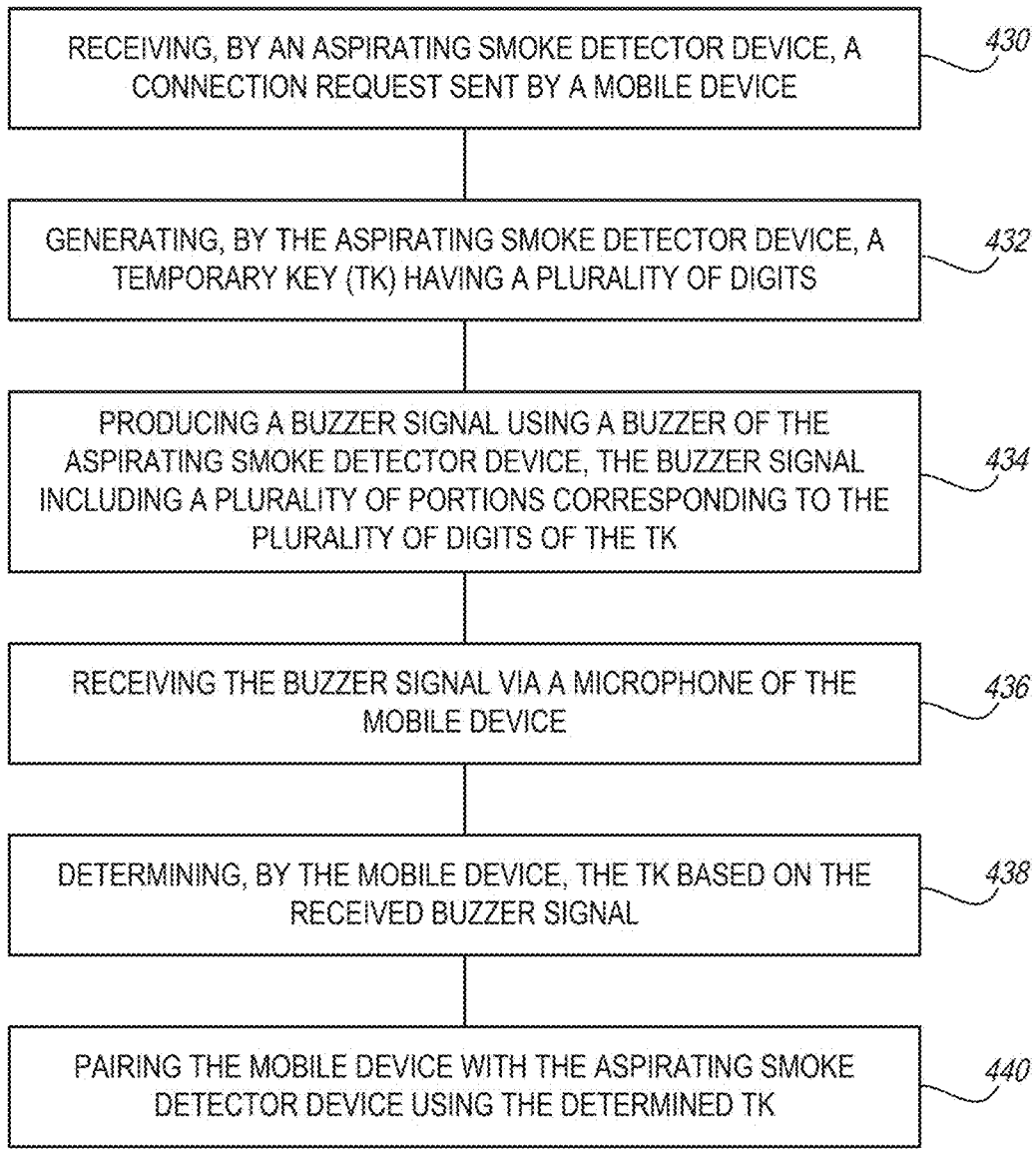
FIG. 4 illustrates a method associated with pairing with an aspirating smoke detector device in accordance with one or more embodiments of the present disclosure.

FIG. 4 illustrates a method associated with pairing with an aspirating smoke detector device in accordance with one or more embodiments of the present disclosure. At 430, the method includes receiving, by an aspirating smoke detector device, a connection request sent by a mobile device. Bluetooth pairing, as known to those of skill in the art, uses a custom key exchange protocol unique to the BLE standard. The devices to be paired exchange a TK and use it to create a Short Term STK which is used to encrypt the connection. The pairing process can be performed in a series of phases shown below. In the first phase, the mobile device 102 sends a connection request to the detector. The two devices then exchange I/O capabilities, authentication requirements, maximum link key size and bonding requirements. Stated differently, the two devices can exchange their capabilities and determine how they are going to go about setting up a secure connection.

At 432, the method includes generating, by the aspirating smoke detector device, a TK having a plurality of digits. As previously discussed, six digits may be generated, though embodiments of the present disclosure do not limit TKs to a particular quantity of digits.

At 434, the method includes producing a buzzer signal using a buzzer of the aspirating smoke detector device, the buzzer signal including a plurality of portions corresponding to the plurality of digits of the TK. In an example where the TK includes six digits, the buzzer produces a signal having six portions. In some embodiments, the portions are separated by intervals of silence. In some embodiments, the portions are separated by an interval of a particular frequency.

At 436, the method includes receiving the buzzer signal via a microphone of the mobile device. At 438, the method includes determining, by the mobile device, the TK based on the received buzzer signal. The sounds received by the microphone can be translated into electrical signals and then the TK can be "reconstructed" by the mobile device. At 440, the method includes pairing the mobile device with the aspirating smoke detector device using the determined TK.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. An aspirating smoke detector device, comprising:
a wireless module;
a piezoelectric buzzer configured to alarm occupants of a facility of a hazard event; and
a controller;
wherein:
the wireless module is configured to receive a connection request from a mobile device; and
the controller is configured to:
generate a temporary key (TK) having a plurality of digits;
cause the buzzer to produce a buzzer signal including a plurality of portions corresponding to the plurality of digits of the TK, wherein the portions are separated by intervals of silence, and wherein durations of the portions are user-configurable;
receive, via the wireless module, an indication of the TK determined by the mobile device based on the buzzer signal;
communicate with the mobile device to complete a pairing with the mobile device using the TK; and
responsive to the completion of the pairing, cause the buzzer to produce another buzzer signal, having a particular frequency, to indicate the completion of the pairing.

2. The device of claim 1, wherein the device does not include a display.

3. The device of claim 1, wherein the plurality of digits of the TK comprise 6 digits and wherein the plurality of portions of the of the buzzer signal comprise 6 portions.

4. The device of claim 1, wherein the controller is configured to generate a random number as the TK.

5. The device of claim 4, wherein the random number includes six digits, and wherein each digit is selected from a group of digits consisting of: zero, one, two, three, four, five, six, seven, eight, and nine.

6. The device of claim 5, wherein the buzzer is configured to buzz at different frequencies.

7. The device of claim 6, wherein the controller is configured to cause the buzzer to:

buzz at a first frequency corresponding to a digit of zero;
buzz at a second frequency corresponding to a digit of one;
buzz at a third frequency corresponding to a digit of two;
buzz at a fourth frequency corresponding to a digit of three;
buzz at a fifth frequency corresponding to a digit of four;
buzz at a sixth frequency corresponding to a digit of five;
buzz at a seventh frequency corresponding to a digit of six;
buzz at an eighth frequency corresponding to a digit of seven;
buzz at a ninth frequency corresponding to a digit of eight; and
buzz at a tenth frequency corresponding to a digit of nine.

8. The device of claim 1, wherein the controller is a microcontroller lacking any security features.

9. A non-transitory machine-readable medium having instructions stored thereon, which when executed by the processor, cause the processor to:
communicate a connection request from a mobile device to an aspirating smoke detector device;
receive a buzzer signal via a microphone of the mobile device, wherein the buzzer signal is produced by a piezoelectric buzzer of the aspirating smoke detector device configured to alarm occupants of a facility of a hazard event, wherein the buzzer signal includes a plurality of portions separated by intervals of silence, and wherein durations of the portions are user-configurable;
determine a temporary key (TK) based on the received buzzer signal; and
pair the mobile device with the aspirating smoke detector device using the TK; and
responsive to a completion of the pairing of the mobile device with the aspirating smoke detector device, receive another buzzer signal, including a particular sequence of buzzes, to indicate the completion of the pairing.

10. The medium of claim 9, wherein the instructions to determine the TK based on the received buzzer signal include instructions to determine a respective frequency of each of the plurality of portions.

11. The medium of claim 10, wherein the instructions to determine the TK based on the received buzzer signal include instructions to compare the determined frequencies of the plurality of portions to a data structure relating a plurality of different frequency ranges to a plurality of TK digits.

12. The medium of claim 11, wherein the data structure includes:
a first frequency range corresponding to a first TK digit;
a second frequency range corresponding to a second TK digit;
a third frequency range corresponding to a third TK digit;
a fourth frequency range corresponding to a fourth TK digit;
a fifth frequency range corresponding to a fifth TK digit;
a sixth frequency range corresponding to a sixth TK digit;
a seventh frequency range corresponding to a seventh TK digit;
an eighth frequency range corresponding to an eighth TK digit;
a ninth frequency range corresponding to a ninth TK digit; and
a tenth frequency range corresponding to a tenth TK digit.

13. The medium of claim 9, including instructions to receive an input to initiate the connection request via a user interface of the mobile device.

14. The medium of claim 13, including instructions to display a notification associated with positioning the microphone of the mobile device with respect to the aspirating smoke detector via the user interface while the buzzer signal is being received.

15. The medium of claim 13, including instructions to display a status of the pairing of the mobile device with the aspirating smoke detector via the user interface.

16. A method for pairing with an aspirating smoke detector device, comprising:
receiving, by an aspirating smoke detector device, a connection request sent by a mobile device;
generating, by the aspirating smoke detector device, a temporary key (TK) having a plurality of digits;
producing a buzzer signal using a piezoelectric buzzer of the aspirating smoke detector device configured to alarm occupants of a facility of a hazard event, the buzzer signal including a plurality of portions corresponding to the plurality of digits of the TK, wherein the plurality of portions are separated by intervals of silence, and wherein durations of the portions are user-configurable;
receiving the buzzer signal via a microphone of the mobile device;
determining, by the mobile device, the TK based on the received buzzer signal; and
pairing the mobile device with the aspirating smoke detector device using the determined TK; and
responsive to a completion of the pairing, producing another buzzer signal using the piezoelectric buzzer of the aspirating smoke detector device to indicate the completion of the pairing, wherein the other buzzer signal has a particular frequency and includes a particular sequence of buzzes.

17. The method of claim 16, wherein the plurality of portions corresponding to the plurality of digits of the TK each include a different frequency.

18. The method of claim 16, wherein generating the TK includes generating the TK using a low speed on-chip oscillator of the aspirating smoke detector device.

19. The method of claim 16, wherein the method includes positioning the mobile device within 30 centimeters of the aspirating smoke detector device while receiving the buzzer signal.

* * * * *